United States Patent
Peterson et al.

(10) Patent No.: US 12,161,994 B2
(45) Date of Patent: Dec. 10, 2024

(54) PROCESS FOR PRODUCING SUPERABSORBENTS

(71) Applicant: BASF SE, Ludwigshafen (DE)

(72) Inventors: Monte Alan Peterson, Freeport, TX (US); John Perry Guentzel, Geismar, LA (US); Juergen Schroeder, Ludwigshafen (DE); Ruediger Funk, Ludwigshafen (DE); Matthias Weismantel, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 844 days.

(21) Appl. No.: 17/289,328

(22) PCT Filed: Nov. 4, 2019

(86) PCT No.: PCT/EP2019/080011
§ 371 (c)(1),
(2) Date: Apr. 28, 2021

(87) PCT Pub. No.: WO2020/099153
PCT Pub. Date: May 22, 2020

(65) Prior Publication Data
US 2022/0016596 A1 Jan. 20, 2022

(30) Foreign Application Priority Data

Nov. 14, 2018 (EP) ..................... 18206113

(51) Int. Cl.
*B01J 20/26* (2006.01)
*A61L 15/60* (2006.01)
(Continued)

(52) U.S. Cl.
CPC ............. *B01J 20/267* (2013.01); *A61L 15/60* (2013.01); *B01J 20/28016* (2013.01);
(Continued)

(58) Field of Classification Search
CPC ................ B01J 20/267; B01J 20/28016; B01J 20/3021; B01J 20/3078; B01J 2220/68;
(Continued)

(56) References Cited

U.S. PATENT DOCUMENTS

| 2011/0021725 A1 | 1/2011 | Takaai et al. |
| 2012/0283401 A1* | 11/2012 | Funk .................. C08F 6/008 |
| | | 526/181 |

(Continued)

FOREIGN PATENT DOCUMENTS

| CN | 101977939 A | 2/2011 |
| CN | 105879803 A | 8/2016 |

OTHER PUBLICATIONS

International Application No. PCT/EP2019/080011, International Search Report and Written Opinion, mailed Dec. 13, 2019.
(Continued)

*Primary Examiner* — Brian D Walck
*Assistant Examiner* — Logan Edward Laclair
(74) *Attorney, Agent, or Firm* — Element IP, PLC

(57) ABSTRACT

The invention relates to a process for producing superabsorbent polymer particles, comprising storing acrylic acid in at least one tank (B1) at a production site for acrylic acid and in at least one tank (B2) at a production site for superabsorbent polymer particles, wherein the at least one tank (B1) at the production site for acrylic acid and the at least one tank (B2) at the production site for superabsorbent polymer particles are interconnected by one single pipe line (3) and the flow inside the pipe line (3) is temporary reversed during interruptions of the production superabsorbent polymer particles.

14 Claims, 1 Drawing Sheet

(51) Int. Cl.
*B01J 20/28* (2006.01)
*B01J 20/30* (2006.01)
*C08F 220/06* (2006.01)

(52) U.S. Cl.
CPC ....... B01J 20/3021 (2013.01); B01J 20/3078 (2013.01); C08F 220/06 (2013.01); *B01J 2220/68* (2013.01)

(58) Field of Classification Search
CPC .......... B01J 4/008; B01J 19/24; B01J 19/245; A61L 15/60; C08F 220/06; C08F 2/02; C08F 2/01
See application file for complete search history.

(56) References Cited

U.S. PATENT DOCUMENTS

| | | |
|---|---|---|
| 2013/0005919 A1 | 1/2013 | Kanzaki et al. |
| 2018/0200691 A1* | 7/2018 | Herfert ................. B01J 20/261 |

OTHER PUBLICATIONS

Graham, et al., "Chapter 3: Commercial Processes for the Manufacture of Superabsorbent Polymers", Modern Superabsorbent Polymer Technology, ed. Buchholz, et al., 2nd Edition, 1998, pp. 69-117.

\* cited by examiner

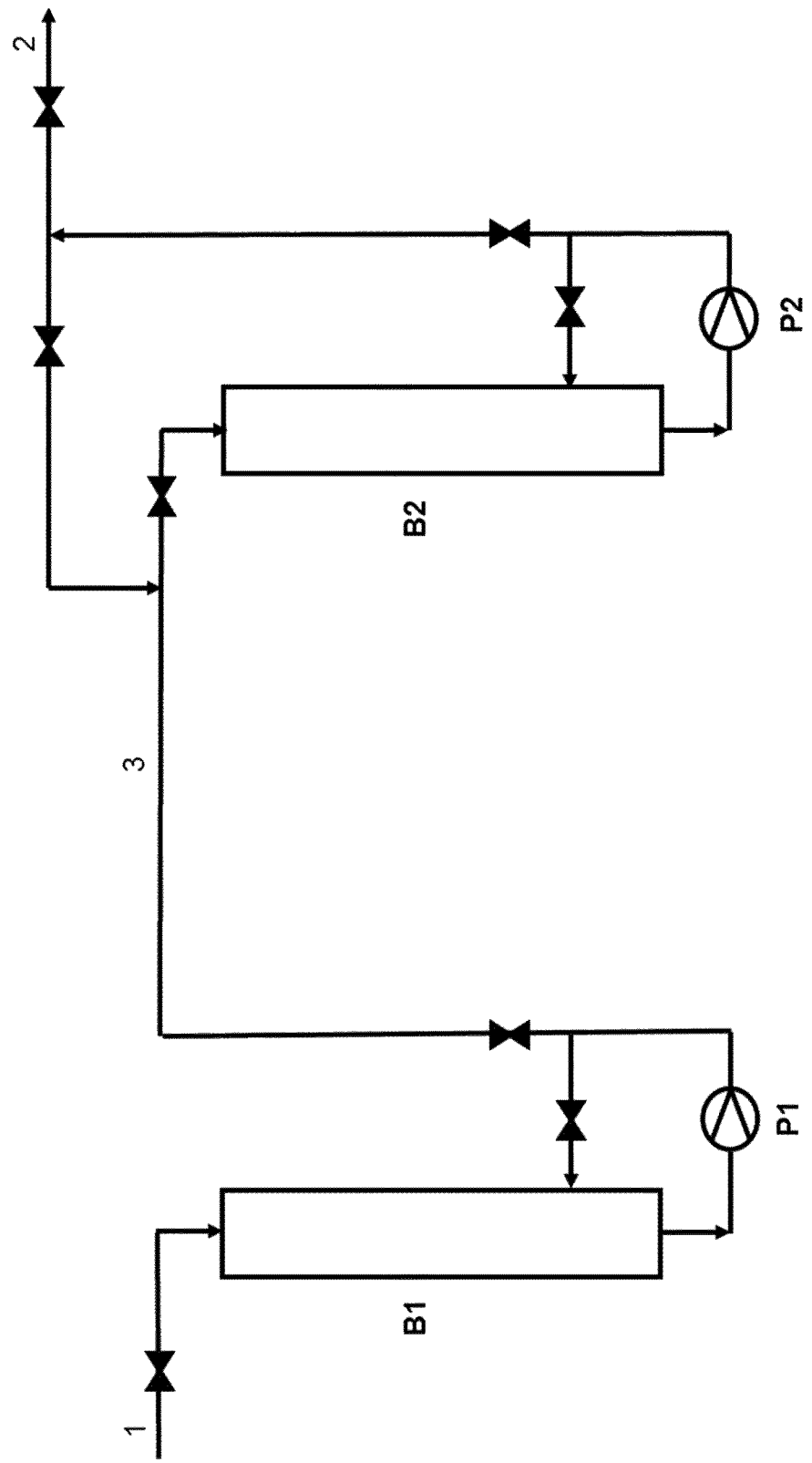

PROCESS FOR PRODUCING SUPERABSORBENTS

CROSS-REFERENCE TO RELATED APPLICATIONS

This is the U.S. national phase of International Application No. PCT/EP2019/080011, filed Nov. 4, 2019, which claims the benefit of European Patent Application No. 18206113.5, filed on Nov. 14, 2018.

DESCRIPTION

The invention relates to a process for producing superabsorbent polymer particles, comprising storing acrylic acid in at least one tank (B1) at a production site for acrylic acid and in at least one tank (B2) at a production site for superabsorbent polymer particles, wherein the at least one tank (B1) at the production site for acrylic acid and the at least one tank (B2) at the production site for superabsorbent polymer particles are interconnected by one single pipe line (3) and the flow inside the pipe line (3) is temporary reversed during interruptions of the production superabsorbent polymer particles.

Superabsorbent polymer particles are used to produce diapers, tampons, sanitary napkins and other hygiene articles, but also as water-retaining agents in market gardening. The superabsorbent polymer particles are often also referred to as "absorbent resin", "superabsorbent", "superabsorbent polymers", "absorbent polymers", "absorbent gelling materials", "hydrophilic polymers" or "hydrogels".

Commercial superabsorbent polymer particles are polymers of partially neutralized acrylic acid as described in the monograph "Modern Superabsorbent Polymer Technology", F. L. Buchholz and A. T. Graham, Wiley-VCH, 1998, pages 69 to 103.

The brochure "Safe Handling and Storage of Acrylic Acid" (EBAM-European Basic Acrylic Monomer Manufacturers Association) discloses guidelines for safe handling of acrylic acid. Draining of pipe lines in case of extended interruptions of recirculation or transfer of acrylic acid is recommended for avoidance of stagnant material.

It was an object of the present invention to provide an improved process for producing superabsorbent polymer particles, especially an improved transport of acrylic acid via pipe lines between different production sites.

The object was achieved by a process for producing superabsorbent polymer particles, comprising polymerization of a monomer solution, comprising
 a) partially neutralized acrylic acid,
 b) at least one crosslinker, and
 c) at least one initiator,
drying the resulting polymer gel, optionally grinding and classifying the resulting dried polymer gel and optionally thermally post-crosslinking and cooling the resulting polymer particles, wherein the partly neutralized acrylic acid is formed by mixing of acrylic acid, an aqueous solution of a base, and optionally water, the acrylic acid to be used is stored in at least one tank (B1) at a production site for acrylic acid and in at least one tank (B2) at a production site for superabsorbent polymer particles and supplied from the at least one tank (B2) at the production site for superabsorbent polymer particles to the neutralization, the at least one tank (B1) at the production site for acrylic acid and the at least one tank (B2) at the production site for superabsorbent polymer particles are interconnected by one single pipe line (3) and the flow inside the pipe line (3) is temporary reversed during interruptions of the production of superabsorbent polymer particles.

FIG. 1 is a schematic diagram of a preferred embodiment of the invention.
 B1 tank at the production site for acrylic acid
 B2 tank at the production site for superabsorbent polymer particles
 P1 pump
 P2 pump
 1 transfer line for acrylic acid to tank B1
 2 transfer line for acrylic acid to neutralization
 3 pipe line between the production site for acrylic acid and the production site for superabsorbent polymer particles The flow inside the pipe line (3) is temporary reversed so that the filling level of the at least one tank (B2) at the production site for superabsorbent polymer particles during interruptions of the production of superabsorbent polymer particles is in a specific range, preferably from 4 to 20%, more preferably from 5 to 15%, most preferably from 6 to 10%.

The present invention is based on the finding that stagnant acrylic acid in pipe lines during extended interruptions of the production of superabsorbent polymer particles can be avoided by reversing the flow until the filing level of the tank (B2) at a production site for superabsorbent polymer particles reaches a predetermined level, again reversing the flow until the filing level of the tank (B2) at a production site for superabsorbent polymer particles reaches a predetermined level, etc. The amount of acrylic acid that is pumped in each cycle should be higher than the hold-up in the pipe line. The use of a ring line, that means two pipe lines between the production site for acrylic acid and the production site for superabsorbent polymer particles, can be avoided. Draining the pipe line during interruptions of the production of superabsorbent polymer particles is also not necessary.

The preferred bases for neutralization are sodium hydroxide, sodium hydrogen carbonate, sodium carbonate, potassium hydroxide, potassium hydrogen carbonate and/or potassium carbonate.

The interruption of the production of superabsorbent polymer particles is preferably at least for 1 h, more preferably for at least 10 h, most preferably for at least 100 h.

It is important that the flow in the pipe line (3) is above a minimum value and the interruptions of the flow in the pipe line (3) are as short as possible.

In one embodiment of the present invention the flow inside the pipe line (3) is preferably at least 0.1 m/s, more preferably at least 0.3 m/s, most preferably at least 0.5 m/s, each with the exception of the time that is needed for changing the direction of the flow.

In one embodiment of the present invention the flow inside the pipe line (3) is preferably at least 0.1 m/s, more preferably at least 0.3 m/s, most preferably at least 0.5 m/s, each for at least 90% of the time of interruption of the production of superabsorbent polymer particles.

The length of the pipe line (3) is preferably from 100 to 20,000 m, more preferably from 500 to 10,000 m, most preferably from 1,000 to 5,000 m. Additional pumps may be required for pipe lines (3) longer than 5,000 m. The inner diameter of the pipe line (3) is preferably from 0.002 to 0.4 m, more preferably from 0.004 to 0.3 m, most preferably from 0.006 to 0.2 m.

The acrylic acid comprises preferably from 0.001 to 0.015% by weight, more preferably from 0.003 to 0.010% by weight, most preferably 0.005 to 0.007% by weight, of a polymerization inhibitor. The preferred polymerization inhibitors are hydroquinone monoethers, for example hydroquinone monomethyl ether.

The temperature of the acrylic acid is preferably from 15 to 35° C., more preferably from 16 to 30° C., most preferably from 17 to 25° C.

The inner volume of the at least one tank (B1) at a production site for acrylic acid and/or the at least one tank (B2) at a production site for superabsorbent polymer particles is preferably from 100 to 2,000 m$^3$, more preferably from 250 to 1,000 m$^3$, most preferably from 500 to 750 m$^3$.

The filling level of the at least one tank (B1) at a production site for acrylic acid and/or the at least one tank (B2) at a production site for superabsorbent polymer particles is preferably from 10 to 80%, more preferably from 15 to 55%, most preferably from 20 to 30%, wherein the filling level is the quotient of the volume of acrylic acid in the tank and the inner volume of the tank.

During interruptions of the production of superabsorbent polymer particles, the filling level of the at least one tank (B2) at a production site for superabsorbent polymer particles is preferably from 4 to 20%, more preferably from 5 to 15%, most preferably from 6 to 10%, wherein the filling level is the quotient of the volume of acrylic acid in the tank and the inner volume of the tank.

The production of the superabsorbents is described in detail hereinafter:

The superabsorbents are produced by polymerizing a monomer solution and are typically water-insoluble.

Acrylic acid typically comprises polymerization inhibitors, preferably hydroquinone monoethers, as storage stabilizers.

Suitable crosslinkers b) are compounds having at least two groups suitable for crosslinking. Such groups are, for example, ethylenically unsaturated groups which can be polymerized free-radically into the polymer chain, and functional groups which can form covalent bonds with the acid groups of acrylic acid. In addition, polyvalent metal salts which can form coordinate bonds with at least two acid groups of acrylic acid are also suitable as crosslinkers b).

Crosslinkers b) are preferably compounds having at least two polymerizable groups which can be polymerized free-radically into the polymer network. Suitable crosslinkers b) are, for example, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, as described in EP 0 530 438 A1, di- and triacrylates, as described in EP 0 547 847 A1, EP 0 559 476 A1, EP 0 632 068 A1, WO 93/21237 A1, WO 2003/104299 A1, WO 2003/104300 A1, WO 2003/104301 A1 and DE 103 31 450 A1, mixed acrylates which, as well as acrylate groups, comprise further ethylenically unsaturated groups, as described in DE 103 31 456 A1 and DE 103 55 401 A1, or crosslinker mixtures, as described, for example, in DE 195 43 368 A1, DE 196 46 484 A1, WO 90/15830 A1 and WO 2002/032962 A2.

The amount of crosslinker b) is preferably 0.05 to 1.5% by weight, more preferably 0.1 to 1% by weight and most preferably 0.3 to 0.6% by weight, based in each case on acrylic acid prior to neutralization. With rising crosslinker content, the centrifuge retention capacity (CRC) falls and the absorption under a pressure of 21.0 g/cm$^2$ passes through a maximum.

The initiators c) used may be all compounds which generate free radicals under the polymerization conditions, for example thermal initiators, redox initiators, photoinitiators. Suitable redox initiators are sodium peroxodisulfate/ascorbic acid, hydrogen peroxide/ascorbic acid, sodium peroxodisulfate/sodium bisulfite and hydrogen peroxide/sodium bisulfite. Preference is given to using mixtures of thermal initiators and redox initiators, such as sodium peroxodisulfate/hydrogen peroxide/ascorbic acid. However, the reducing component used is preferably disodium 2-hydroxy-2-sulfonatoacetate or a mixture of disodium 2-hydroxy-2-sulfinatoacetate, disodium 2-hydroxy-2-sulfonatoacetate and sodium bisulfite. Such mixtures are obtainable as Brüggolite® FF6 and Brüggolite® FF7 (Brüggemann Chemicals; Heilbronn; Germany).

Typically, an aqueous monomer solution is used. The water content of the monomer solution is preferably from 40 to 75% by weight, more preferably from 45 to 70% by weight and most preferably from 50 to 65% by weight. It is also possible to use monomer suspensions, i.e. monomer solutions with excess sodium acrylate. With rising water content, the energy requirement in the subsequent drying rises, and, with falling water content, the heat of polymerization can only be removed inadequately.

For optimal action, the preferred polymerization inhibitors require dissolved oxygen. The monomer solution can therefore be freed of dissolved oxygen before the polymerization by inertization, i.e. flowing an inert gas through, preferably nitrogen or carbon dioxide. The oxygen content of the monomer solution is preferably lowered before the polymerization to less than 1 ppm by weight, more preferably to less than 0.5 ppm by weight, most preferably to less than 0.1 ppm by weight.

For better control of the polymerization reaction, it is optionally possible to add all known chelating agents to the monomer solution or suspension or to the raw materials thereof. Suitable chelating agents are, for example, phosphoric acid, diphosphoric acid, triphosphoric acid, polyphosphoric acid, citric acid, tartaric acid, or salts thereof.

The monomer solution is polymerized. Suitable reactors are, for example, kneading reactors or belt reactors. In the kneader, the polymer gel formed in the polymerization of an aqueous monomer solution or suspension is comminuted continuously by, for example, contrarotatory stirrer shafts, as described in WO 2001/038402 A1. Polymerization on the belt is described, for example, in DE 38 25 366 A1 and U.S. Pat. No. 6,241,928. Polymerization in a belt reactor forms a polymer gel which has to be comminuted in a further process step, for example in an extruder or kneader.

To improve the drying properties, the comminuted polymer gel obtained by means of a kneader can additionally be extruded.

The acid groups of the resulting polymer gels have typically been partially neutralized. Neutralization is carried out at the monomer stage. This is typically accomplished by mixing in the neutralizing agent as an aqueous solution or preferably also as a solid. The degree of neutralization is preferably from 40 to 85 mol %, more preferably from 50 to 80 mol % and most preferably from 60 to 75 mol %, for which the customary neutralizing agents can be used, preferably alkali metal hydroxides, alkali metal oxides, alkali metal carbonates or alkali metal hydrogencarbonates and also mixtures thereof. Instead of alkali metal salts, it is also possible to use ammonium salts. Particularly preferred alkali metals are sodium and potassium, but very particular preference is given to sodium hydroxide, potassium hydroxide and also mixtures thereof.

The resulting polymer gel is dried. The driers are not subject to any restriction. However, the drying of the polymer gel is preferably performed with a belt drier until the residual moisture content is preferably 0.5 to 10% by weight, more preferably 1 to 7% by weight and most preferably 2 to 5% by weight, the residual moisture content being determined by EDANA recommended test method No. WSP 230.2 (05) "Mass Loss Upon Heating". In the case of a too high residual moisture content, the dried polymer gel has a too low glass transition temperature $T_g$ and can be processed further only with difficulty. In the case of a too low residual moisture content, the dried polymer gel is too brittle and, in the subsequent grinding steps, undesirably large amounts of polymer particles with an excessively low particle size are obtained ("fines"). The solids content of the gel before the drying is preferably from 25 to 90% by weight, more preferably from 35 to 70% by weight and most preferably from 40 to 60% by weight. However, a fluidized bed drier or a paddle drier may optionally also be used for drying purposes.

Subsequently, the dried polymer gel is ground and classified. The apparatus used for grinding may typically be single- or multistage roll mills, preferably two- or three-stage roll mills, pin mills, hammer mills or vibratory mills.

The mean particle size of the polymer particles removed as the product fraction is preferably at least 200 µm, more preferably from 250 to 600 µm and very particularly from 300 to 500 µm. The mean particle size of the product fraction may be determined by means of EDANA recommended test method No. WSP 220.2 (05) "Particle Size Distribution", where the proportions by mass of the screen fractions are plotted in cumulated form and the mean particle size is determined graphically. The mean particle size here is the value of the mesh size which gives rise to a cumulative 50% by weight.

To improve the properties, the polymer particles may subsequently be thermally surface post-crosslinked. Suitable surface post-crosslinkers are compounds which comprise groups which can form covalent bonds with at least two acid groups of the polymer particles. Suitable compounds are, for example, polyfunctional amines, polyfunctional amido amines, polyfunctional epoxides, as described in EP 0 083 022 A2, EP 0 543 303 A1 and EP 0 937 736 A2, di- or polyfunctional alcohols, as described in DE 33 14 019 A1, DE 35 23 617 A1 and EP 0 450 922 A2, or 3-hydroxyalkylamides, as described in DE 102 04 938 A1 and U.S. Pat. No. 6,239,230.

The amount of surface post-crosslinker is preferably 0.001 to 2% by weight, more preferably 0.02 to 1% by weight and most preferably 0.05 to 0.2% by weight, based in each case on the polymer particles.

In a preferred embodiment of the present invention, polyvalent cations are applied to the particle surface in addition to the surface post-crosslinkers before, during or after the surface post-crosslinking.

The polyvalent cations usable in the process according to the invention are, for example, divalent cations such as the cations of zinc, magnesium, calcium, iron and strontium, trivalent cations such as the cations of aluminum, iron, chromium, rare earths and manganese, tetravalent cations such as the cations of titanium and zirconium. Possible counterions are chloride, bromide, hydroxide, sulfate, hydrogensulfate, carbonate, hydrogencarbonate, nitrate, phosphate, hydrogenphosphate, dihydrogenphosphate and carboxylate, such as acetate and lactate. Aluminum hydroxide, aluminum sulfate and aluminum lactate are preferred. Apart from metal salts, it is also possible to use polyamines as polyvalent cations.

The amount of polyvalent cation used is, for example, 0.001 to 1.5% by weight, preferably 0.005 to 1% by weight and more preferably 0.02 to 0.8% by weight, based in each case on the polymer particles.

The surface post-crosslinking is typically performed in such a way that a solution of the surface post-crosslinker is sprayed onto the dried polymer particles. After the spray application, the polymer particles coated with surface post-crosslinker are dried thermally, and the surface post-crosslinking reaction can take place either before or during the drying.

The spray application of a solution of the surface post-crosslinker is preferably performed in mixers with moving mixing tools, such as screw mixers, disk mixers and paddle mixers. Particular preference is given to horizontal mixers such as paddle mixers, very particular preference to vertical mixers. The distinction between horizontal mixers and vertical mixers is made by the position of the mixing shaft, i.e. horizontal mixers have a horizontally mounted mixing shaft and vertical mixers a vertically mounted mixing shaft. Suitable mixers are, for example, horizontal Pflugschar® plowshare mixers (Gebr. Lödige Maschinenbau GmbH; Paderborn; Germany), Vrieco-Nauta continuous mixers (Hosokawa Micron BV; Doetinchem; the Netherlands), Processall Mixmill mixers (Processall Incorporated; Cincinnati; USA) and Schugi Flexomix® (Hosokawa Micron BV; Doetinchem; the Netherlands). However, it is also possible to spray on the surface post-crosslinker solution in a fluidized bed.

The surface post-crosslinkers are typically used in the form of an aqueous solution. The penetration depth of the surface post-crosslinker into the polymer particles can be adjusted via the content of non-aqueous solvent and total amount of solvent.

The thermal surface post-crosslinking is preferably performed in contact driers, more preferably paddle driers, most preferably disk driers. Suitable driers are, for example, Hosokawa Bepex® Horizontal Paddle Dryer (Hosokawa Micron GmbH; Leingarten; Germany), Hosokawa Bepex® Disc Dryer (Hosokawa Micron GmbH; Leingarten; Germany) and Nara Paddle Dryer (NARA Machinery Europe; Frechen; Germany). Moreover, fluidized bed driers may also be used.

The thermal surface post-crosslinking can be effected in the mixer itself, by heating the jacket or blowing in warm air. Equally suitable is a downstream drier, for example a shelf drier, a rotary tube oven or a heatable screw. It is particularly advantageous to effect mixing and drying in a fluidized bed drier.

Preferred surface post-crosslinking temperatures are in the range of 100 to 250° C., preferably 110 to 220° C., more preferably 120 to 210° C. and most preferably 130 to 200° C. The preferred residence time at this temperature in the reaction mixer or drier is preferably at least 10 minutes, more preferably at least 20 minutes, most preferably at least 30 minutes, and typically at most 60 minutes.

Subsequently, the surface post-crosslinked polymer particles can be classified again, excessively small and/or excessively large polymer particles being removed and recycled into the process.

To further improve the properties, the surface post-crosslinked polymer particles can be coated or remoisturized.

The remoisturizing is preferably performed at 30 to 80° C., more preferably at 35 to 70° C., most preferably at 40 to 60° C. At excessively low temperatures, the superabsorbents tend to form lumps, and, at higher temperatures, water already evaporates to a noticeable degree. The amount of water used for remoisturizing is preferably from 1 to 10% by weight, more preferably from 2 to 8% by weight and most preferably from 3 to 5% by weight. The remoisturizing increases the mechanical stability of the polymer particles and reduces their tendency to static charging.

Suitable coatings for improving the free swell rate and the saline flow conductivity (SFC) are, for example, inorganic inert substances, such as water-insoluble metal salts, organic polymers, cationic polymers and di- or polyvalent metal cations. Suitable coatings for dust binding are, for example, polyols. Suitable coatings for counteracting the undesired caking tendency of the polymer particles are, for example, fumed silica, such as Aerosil® 200, or precipitated silica, such as Sipernat® D17, and surfactants, such as Span® 20.

The present invention further provides hygiene articles, comprising superabsorbent polymer particles prepared according to the inventive process.

EXAMPLE

A production site for acrylic acid and a production site for superabsorbent polymer particles were interconnected by a pipe line (3) having a length of 3,200 m and an inner diameter of 0.0762 m.

The inner volume of the tank B1 at the production site for acrylic acid was 534 $m^3$ and the inner volume of the tank B2 at the production site for superabsorbent polymer particles was 534 $m^3$ The acrylic acid comprised 0.005% by weight of hydroquinone monomethyl ether and had a temperature of 18 to 24° C.

The production of superabsorbent polymer particles was interrupted for 70 h. The filling level in tank B2 at the production site for superabsorbent polymer particles was reduced to 15% prior to stopping the production of superabsorbent polymer particles by reducing the feed from tank B1 to tank B2. The minimum flow in the pipe line (3) was 0.6 m/s. Next, the flow inside the pipe line (3) was reversed. The flow inside the pipe line (3) was 0.6 m/s. As the filling level in tank B2 at the production site for superabsorbent polymer particles was decreased to 5%, the flow inside the pipe line (3) was reversed again. These steps were repeated so that the filling level interruptions of the production of superabsorbent polymer particles was hold in the range from approx. 5 to approx. 15%. The filling level interruptions of the production of superabsorbent polymer particles was increased to 25% prior to starting the production of superabsorbent polymer particles again by increasing the feed from tank B1 to tank B2.

Preparation of Superabsorbent Polymer Particles

By continuously mixing deionized water, 48% by weight sodium hydroxide solution and acrylic acid, an acrylic acid/sodium acrylate solution was prepared, such that the degree of neutralization corresponds to 72.4 mol %. The solids content of the monomer solution was 40.0% by weight.

The monomer solution was further cooled. Next, 3-tuply ethoxylated glycerol triacrylate was added as crosslinker to the monomer solution. The amount of crosslinker was 1.43 kg per t of monomer solution.

The free-radical polymerization was initiated by adding 1.31 kg of a 0.25% by weight aqueous hydrogen peroxide solution, 3.00 kg of a 30% by weight aqueous sodium peroxodisulfate solution, and 0.98 kg of a 1% by weight aqueous ascorbic acid solution, each based per t of monomer solution. The peroxides were added to the monomer solution.

The throughput of the monomer solution was 21 t/h. The monomer solution had a temperature of 26° C. at the feed.

The components (monomer solution and aqueous ascorbic acid solution) were metered continuously into a continuous kneader reactor with a capacity of 6.3 $m^3$ (LIST AG, Arisdorf, Switzerland).

Between the addition point for the crosslinker and the addition points of the peroxides, the monomer solution was inertized with nitrogen.

After approx. 50% of the residence time in the polymerization reactor, a metered addition of fines (1270 kg/h), which were obtained from the production process by grinding and screening, to the reactor additionally took place. The residence time of the reaction mixture in the reactor was 15 minutes.

The resulting polymer gel was placed onto a belt dryer. On the belt dryer, an air/gas mixture flowed continuously around the polymer gel and dried it.

The dried polymer gel was ground and screened off to a particle size fraction of 150 to 850 μm.

The invention claimed is:

1. A process for producing superabsorbent polymer particles, comprising polymerizing a monomer solution, comprising
    a) partially neutralized acrylic acid,
    b) at least one crosslinker, and
    c) at least one initiator,
    drying a resulting polymer gel, optionally grinding and classifying a resulting dried polymer gel and optionally thermally post-crosslinking and cooling resulting polymer particles, wherein the partly neutralized acrylic acid is formed by mixing acrylic acid, an aqueous solution of a base, and optionally water, the acrylic acid used is stored in at least one tank (B1) at a production site for acrylic acid and in at least one tank (B2) at a production site for superabsorbent polymer particles and supplied from the at least one tank (B2) at the production site for superabsorbent polymer particles to the neutralization, the at least one tank (B1) at the production site for acrylic acid and the at least one tank (B2) at the production site for superabsorbent polymer particles are interconnected by one single pipe line (3) and a flow inside the pipe line (3) is temporarily reversed during an interruption of the production of superabsorbent polymer particles,
    thereby avoiding stagnant acrylic acid in pipe lines during an extended interruption in production of the superabsorbent polymer particles.

2. The process according to claim 1, wherein the a base for neutralization is sodium hydroxide, sodium hydrogen carbonate, sodium carbonate, potassium hydroxide, potassium hydrogen carbonate, and/or potassium carbonate.

3. The process according to claim 1, wherein the interruption of the production of superabsorbent polymer particles is at least for 1 h.

4. The process according to claim 1, wherein the flow in the pipe line (3) is at least 0.1 m/s for at least 90% of the time of the interruption of the production of superabsorbent polymer particles.

5. The process according to claim 1, wherein the flow in the pipe line (3) is at least 0.5 m/s for at least 90% of the time of the interruption of the production of superabsorbent polymer particles.

6. The process according to claim 1, wherein the flow inside the pipe line (3) is at least 0.1 m/s with an exception of time needed for changing the direction of the flow.

7. The process according to claim 1, wherein the flow inside the pipe line (3) is at least 0.5 m/s with an exception of time needed for changing the direction of the flow.

8. The process according to claim 1, wherein a length of the pipe line (3) is from 100 to 20,000 m.

9. The process according to claim 1, wherein a length of the pipe line (3) is from 1000 to 5,000 m.

10. The process according to claim 1, wherein an inner diameter of the pipe line (3) is from 0.002 to 0.4 m.

11. The process according to claim 1, wherein the acrylic acid comprises from 0.001 to 0.015% by weight of a polymerization inhibitor.

12. The process according to claim 1, wherein a temperature of the acrylic acid is from 15 to 25° C.

13. The process according to claim 1, wherein an inner volume of at least one of the tanks is from 100 to 2000 m$^3$.

14. The process according to claim 1, wherein a filling level of at least one of the tanks is from 10 to 80%, wherein the filling level is the quotient of a volume of acrylic acid in the tank and an inner volume of the tank.

\* \* \* \* \*